(12) United States Patent
Pui et al.

(10) Patent No.: US 6,230,572 B1
(45) Date of Patent: May 15, 2001

(54) INSTRUMENT FOR MEASURING AND CLASSIFYING NANOMETER AEROSOLS

(75) Inventors: David Y. H. Pui, Plymouth; Da-Ren Chen, Roseville; Frederick R. Quant, Shoreview; Gilmore J. Sem, Lauderdale, all of MN (US); Heinz Fissan, Kerken; Detlef Hummes, Duisburg, both of (DE); Frank Dorman, Minneapolis, MN (US)

(73) Assignee: TSI Incorporated, St. Paul, MN (US)

(*) Notice: Subject to any disclaimer, the term of this patent is extended or adjusted under 35 U.S.C. 154(b) by 0 days.

(21) Appl. No.: 09/249,723

(22) Filed: Feb. 12, 1999

Related U.S. Application Data

(60) Provisional application No. 60/074,589, filed on Feb. 13, 1998.

(51) Int. Cl.$^7$ .................................................... G01N 1/00
(52) U.S. Cl. ............................................................ 73/863.21
(58) Field of Search ........................... 73/863.21, 864.81, 73/28.04, 865.5; 250/288; 356/335, 336, 440; 324/71.4; 96/15, 62

(56) References Cited

U.S. PATENT DOCUMENTS

| | | | |
|---|---|---|---|
| 4,699,710 | 10/1987 | Williams | 209/24 |
| 4,790,650 | * 12/1988 | Keady . | |
| 5,098,657 | 3/1992 | Blackford et al. | 422/73 |
| 5,251,762 | 10/1993 | Taylor et al. | 209/127.4 |
| 5,542,543 | 8/1996 | Yasukuni | 209/127.1 |
| 5,596,136 | * 1/1997 | Flagan et al. . | |
| 5,869,831 | 2/1999 | De La Mora et al. | 250/288 |

FOREIGN PATENT DOCUMENTS 1114472    9/1984    (SU) .

OTHER PUBLICATIONS

"Model 3934 Scanning Mobility Particle Sizer" Product Information, TSI Incorporated, No Date.

"Model 3071A Electrostatic Classifier" Product Information, TSI Incorporated, No Date.

Model 3940 Submicrometer Monodisperse Aerosol Generation System:, Product Information TSI Incorporated, No Date.

"Aerosol Classification by Electric Mobility: Apparatus, Theory, and Applications," *Journal Aerosol Science*, 1975 pp. 443–451, W.O. Knutson and K.T. Whitby.

(List continued on next page.)

*Primary Examiner*—Robert Raevis
(74) *Attorney, Agent, or Firm*—Larkin, Hoffman, Daly & Lindgren, Ltd.; Frederick W. Niebuhr, Esq

(57) ABSTRACT

An apparatus for classifying polydisperse aerosols includes aerosol and sheath gas conduits for conducting a sample aerosol and a sheath gas toward a merger area. At the merger area the sheath gas and about ten percent of the sample aerosol merge, then travel through a differential mobility analyzer (DMA) and along a tubular electrode of the DMA. Selected particles, i.e. particles having electrical mobilities within a narrow range, pass through a collection aperture of the electrode. The DMA output, an aerosol consisting of the selected particles, is provided to a condensation particle counter or other device for determining the aerosol concentration. The remainder of the sample aerosol is conducted away from the merger area along a bypass flow conduit. The bypass flow and an improved aerodynamic design provide for a slit at the merger area that is sufficiently narrow to minimize unwanted electric field penetration at the slit and DMA entrance. An annular flow restriction feature in the bypass conduit promotes and maintains laminar, uniform-velocity flow near the slit. The collection aperture is located medially along the tubular electrode, to prevent electrical field fringing near the aperture.

40 Claims, 13 Drawing Sheets

OTHER PUBLICATIONS

"Nanometer Differential Mobility Analyzer (Nano–DMA): Design and Numerical Modeling," *Journal Aerosol Science*, vol. 27, Suppl. 1., pp. 5137–5138, 1996, Daren Chen, David Y.H.Pui, D. Hummes, H.Fissan, F.R. Quant, G.J. Sem.

"A Submicron Aerosol Standard and the Primary, Absolute Calibration of the Condensation Nuclei Counter", Benjamin Y.H. Liu, David Y.H. Pui,*Journal of Colloid and Interface Science*, vol. 47, No. 1, Apr. 1974.

"Experimental Comparison of Four Differential Mobility Analyzers for Nanometer Aerosol Measurements"; H.Fissan,, D. Hummes, F. Stratmann, P. Buscher and S. Neumann, D. Y.H. Pui, D. Chen, *Aerosal Science and Technology* 24:1–13 (1996).

"Nanometer Differential Mobility Analyzer (Nano–DMA): Experimental Evaluation and Performance Verification"; *Journal Aerosal Science*, vol. 27, Suppl. 1, pp. S135–S136, 1996 D. Hummes,S. Neumann, H. Fissan, D.R. Chen, D.Y. H. Pui, F.R. Quant and G. J. Sem.

* cited by examiner

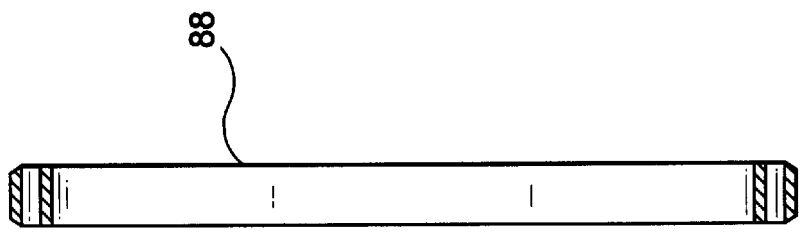
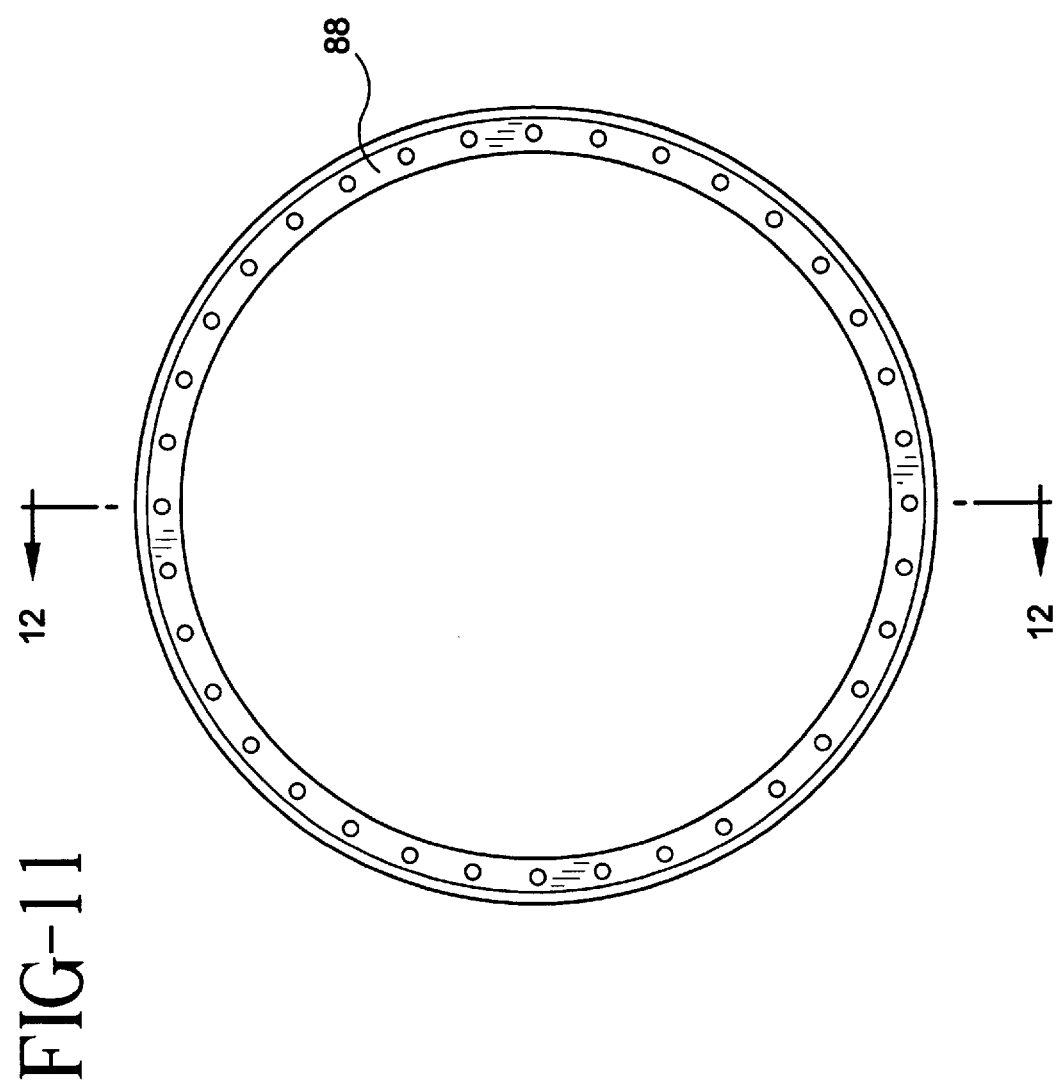

INSTRUMENT FOR MEASURING AND CLASSIFYING NANOMETER AEROSOLS

This application claims the benefit of Provisional Application No. 60/074,589 entitled "Instrument For Measuring and Classifying Nanometer Aerosols" filed Feb. 13, 1998.

BACKGROUND OF THE INVENTION

The present invention relates to devices and systems for analyzing aerosols, and more particularly to instruments used to classify particles or other elements suspended in the aerosols according to their electrical mobility, size or other chosen characteristics.

A variety of devices have been developed for analyzing aerosols, particularly as to the particles or droplets suspended in the gaseous media (usually air) of the aerosols. Among these are differential mobility analyzers and electrical precipitators, which distinguish suspended elements of aerosols based on their electrical mobility. Since electrical mobility is inversely related to the size of the particle or other element, the DMA and precipitator effectively distinguish suspended elements according to size.

Other devices distinguish among particles based on particle mass and shape, scattered light, or diffusion, rather than electrical mobility. These include impactors, cyclones, horizontal elutriators and centrifugal separators.

Recent technological advances and discoveries have generated a strong interest in analyzing extremely fine particles, i.e. particles with diameters in the nanometer range. Certain "nanophase" materials composed of nanometer particles have been found to possess enhanced mechanical, optical and electrical/magnetic properties desired for advanced engineering applications. Semiconductor fabrication requires the control of nanometer particles. With the feature sizes in state-of-the-art devices at or below 0.35 micrometers, the need for micro contamination control must take into account particles smaller than about 35 nanometers in diameter. In magnetic disk drives, the distance between the aerodynamically supported transducing head and rigid disk is being reduced into the submicron range to allow more dense storage of magnetic data. In analytical chemistry, the study of aerosols to detect macro molecules in the nanometer range is increasingly accepted. Nanometer particles are suspected carcinogens which can penetrate deeply into lungs and are difficult to remove by lung clearing mechanisms. Accordingly, these particles increasingly are the subject of industrial hygiene and epidemiology studies, and the need for nanometer aerosol filtration is receiving increased attention. Photochemical reactions monitored in air pollution studies often begin with nanometer particles. In nucleation and condensation processes, nanometer particles serve as the incipient nuclei. Accordingly, aerosol element sizing instruments are being evaluated for their capacity to distinguish particles and other elements in the nanometer size range.

The differential mobility analyzer, (DMA) has shown the greatest potential for measuring nanometer aerosols. However, at sizes below about 20 nanometers, presently available differential mobility analyzers experience a deterioration in size resolution and detection sensitivity due to particle Brownian motion. More particularly, diffusional losses in the aerosol transport passages reduce detection sensitivity, and a broadening of the transfer function due to diffusion becomes pronounced at sizes below ten nanometers, which reduces resolution.

Resolution also is limited by a mismatch in the aerosol and sheath flows at the entrance to the classifying region of the DMA. The flow mismatch causes undesirable recirculation near the entrance, and becomes worse when the DMA is operated at high flow ratios (sheath flow: aerosol flow).

Undesirable electrical field effects also have more of an impact on nanometer particles. At the entrance to the classifying region is a slit that is sufficiently wide to allow an electric field to penetrate into the aerosol passage upstream of the slit. Also, use of an insulator near the high voltage electrode leads to a surface electric field effect that causes aerosol loss and electric field fringing around the monodisperse exit.

Accordingly, it is an object of the present invention to provide a differential mobility analyzer or other aerosol analyzing instrument in which the time of transfer through the aerosol transport passages is considerably reduced, thereby minimizing diffusion.

Another object is to provide a system capable of segregating and analyzing suspended particles in aerosols, particularly elements with diameters below ten nanometers, with increased sensitivity and higher resolution.

A further object is to provide a differential mobility analyzer less susceptible to undesirable electric field effects.

Yet another object is to provide a more compact and efficient DMA design.

SUMMARY OF THE INVENTION

To achieve these and other objects, there is provided an apparatus for classifying a polydisperse aerosol. The apparatus includes a sample aerosol conduit adapted to receive a sample aerosol consisting essentially of a polydisperse suspension of particles in a gaseous medium. The conduit further is adapted to conduct the sample aerosol in a substantially non-turbulent flow toward a merger area. A sheath gas conduit is provided to conduct a filtered sheath gas in a substantially non-turbulent flow towards the merger area. Both conduits are open to the merger area. A particle segregation device is disposed in fluid communication with the merger area, to receive a merged aerosol comprising the sheath gas and a first portion of the sample aerosol. The segregation device is further adapted for segregating the particles suspended in the merged aerosol according to their electrical mobility, thus to provide a selected aerosol consisting essentially of selected ones of the particles that exhibit electrical mobilities within a selected range. An aerosol bypass conduit is in fluid communicated with the sample aerosol conduit. The aerosol bypass conduit receives a second portion of the sample aerosol proximate the merger area and conducts the second portion of the sample aerosol away from the particle segregation device. A flow restricting feature, comprised of a body having passages therethrough, is disposed in the aerosol bypass conduit at a location downstream from the merger area. The restricting feature restricts fluid flow at the downstream location, thereby tending to equalize a flow volocity of the sample aerosol through the sample aerosol conduit upstream of the restricting feature.

In this application, the term "particle" is used in a broad sense known in the art, i.e., to encompass airborne materials in the form of solid matter, liquid matter, or clusters of molecules consisting of a combination of solid, liquid and/or gaseous matter. The term "aerosol" refers to a gaseous medium and the particles suspended in the medium.

Preferably, the sheath gas and aerosol flows are not only non-turbulent, but laminar. Moreover, the first portion of the sample aerosol preferably is small in proportion to the sample aerosol in terms of volume and flow rate. For example, the sample aerosol flow rate can be about 15 liters per minute (lpm) while the first portion of the sample aerosol can have a flow rate of about 1.5 lpm. As a result, the aerosol can be drawn through the sample aerosol conduit at a lower linear speed that facilities a more laminar flow, yet provide a sufficient volume (of the first portion) for merger with the sheath flow. The bypass conduit allows a smooth egress from the merger area, avoiding recirculation or other turbulence at the inlet to the classifying region. The excess aerosol can be exhausted, or filtered and used as part of the sheath air input.

Because of the bypass conduit, the sample aerosol can traverse the sample aerosol conduit in about 1/10th the time required in previous designs, for a significant reduction in diffusion loss of nanometer particles. At a nominal particle diameter of 3 nanometers, diffusion losses are about 1/3 the losses experienced in previous devices. The length of the classifying region can be reduced, to further reduce diffusion broadening.

The preferred particle segregation device is a differential mobility analyzer of a cylindrical configuration, with a passage to accommodate a flow of the merged aerosol therethrough. An electrically conductive electrode is disposed along the passage, and is electrically biased to attract oppositely charged elements suspended in the merged aerosol flowing along the electrode. A collection aperture is formed in the electrode for receiving the selected elements. Preferably the electrode is tubular, and the aperture is formed through the tubular electrode wall along a medial region of the electrode. Thus, a substantial portion of the electrode extends downstream of the collection aperture. As a result, the electrical field is more uniform over the entire classifying region. An insulator between the biased electrode and the device exterior is positioned in radially spaced-apart relation to the tubular electrode, eliminating undesirable electric field fringing near the collection aperture.

Advantageously, an electrically conductive cylindrical flow guide can be mounted inside of the electrode, extending downstream from the collection aperture. The flow guide is electrically coupled to the electrode, which virtually eliminates electrostatic losses as the aerosol flows between the electrode and the flow guide exterior. In a further enhancement, the flow guide is tubular, and accommodates a flow of sheath gas to provide part of the sheath gas conduit. The guide can be symmetrical about a vertical axis, with the sample aerosol provided downwardly along the axis in an annular laminar flow. At the same time, sheath gas is provided upwardly along the axis, radially outward and downwardly in an annular flow surrounded by the annular sample aerosol flow, with both flows proceeding toward the merger location.

Thus in accordance with the present invention, nanometer particles and other elements can be selected and classified with increased detection sensitivity and higher resolution, primarily by a considerable reduction in diffusion and electrostatic losses. The use of the bypass conduit insures a sufficient volume of a sample aerosol without a substantial pressure drop or higher linear speed, thus to insure a more laminar flow of the aerosol to the classifying region. The classifying region is reduced in length and undesirable electric field effects are removed, further enhancing the reliability of results obtained.

IN THE DRAWINGS

For a further understanding of the above and other features and advantages, references made to the following detailed description and to the drawings, in which.

Figure 9:
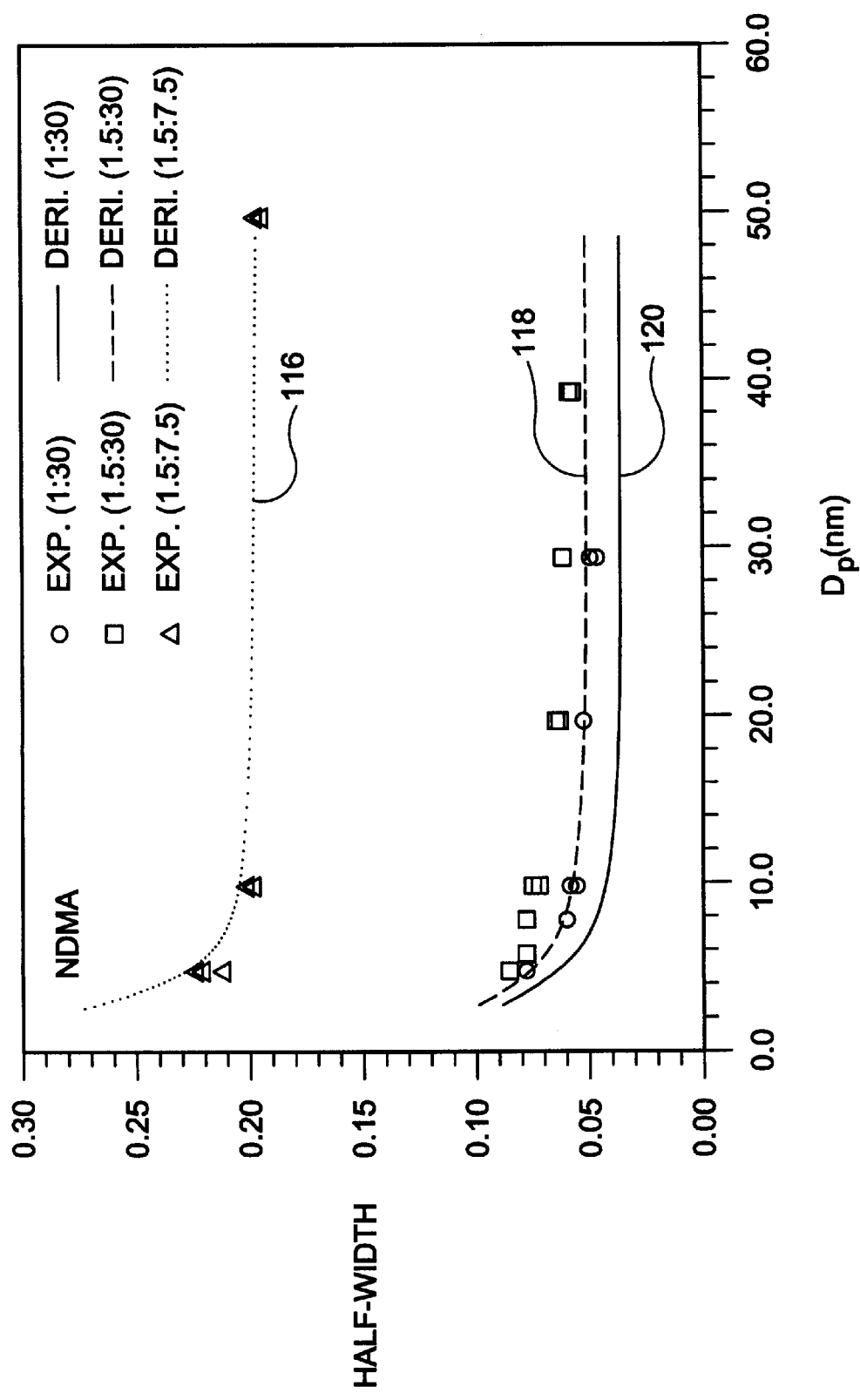
Figure 10:
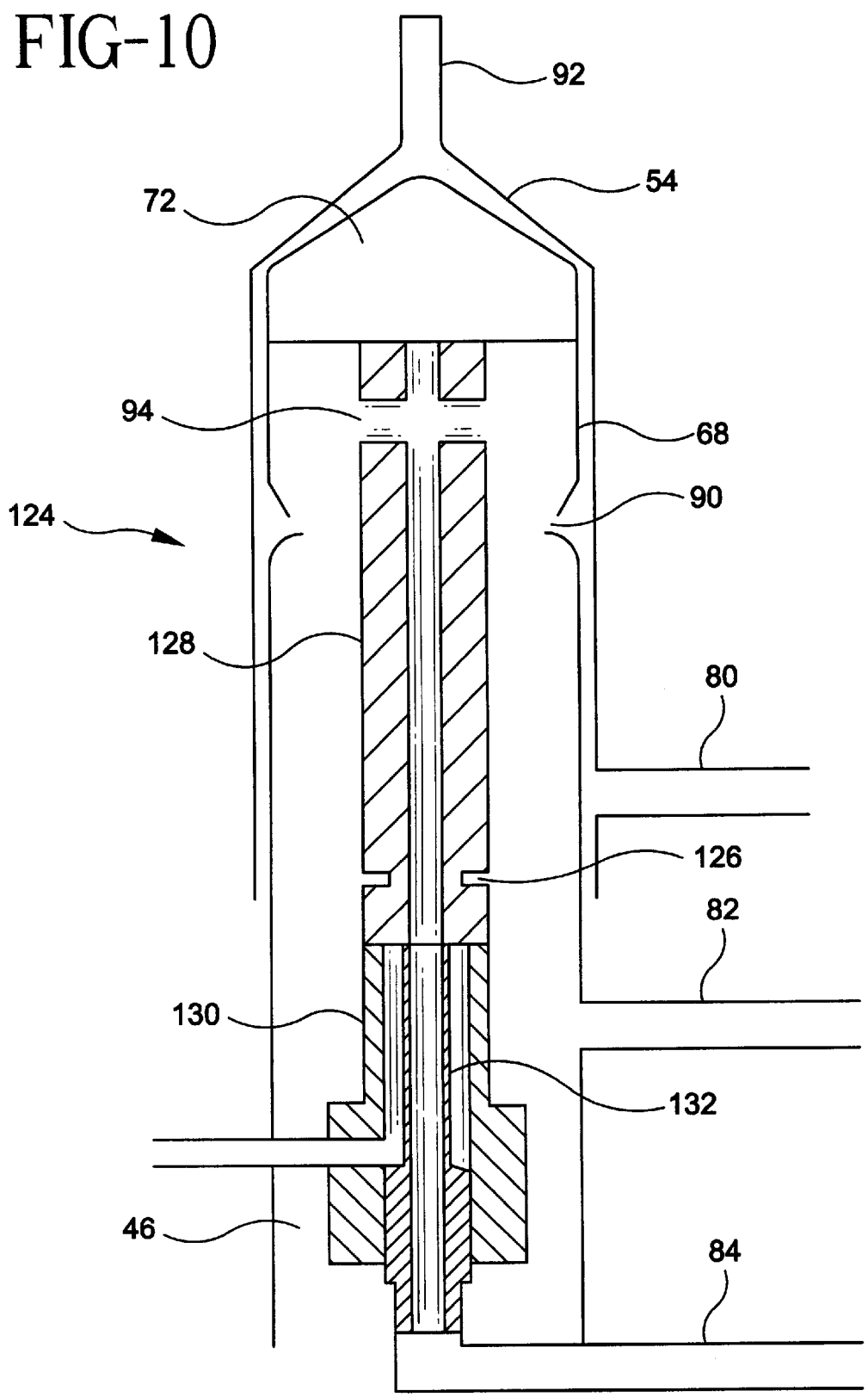
Figure 13:
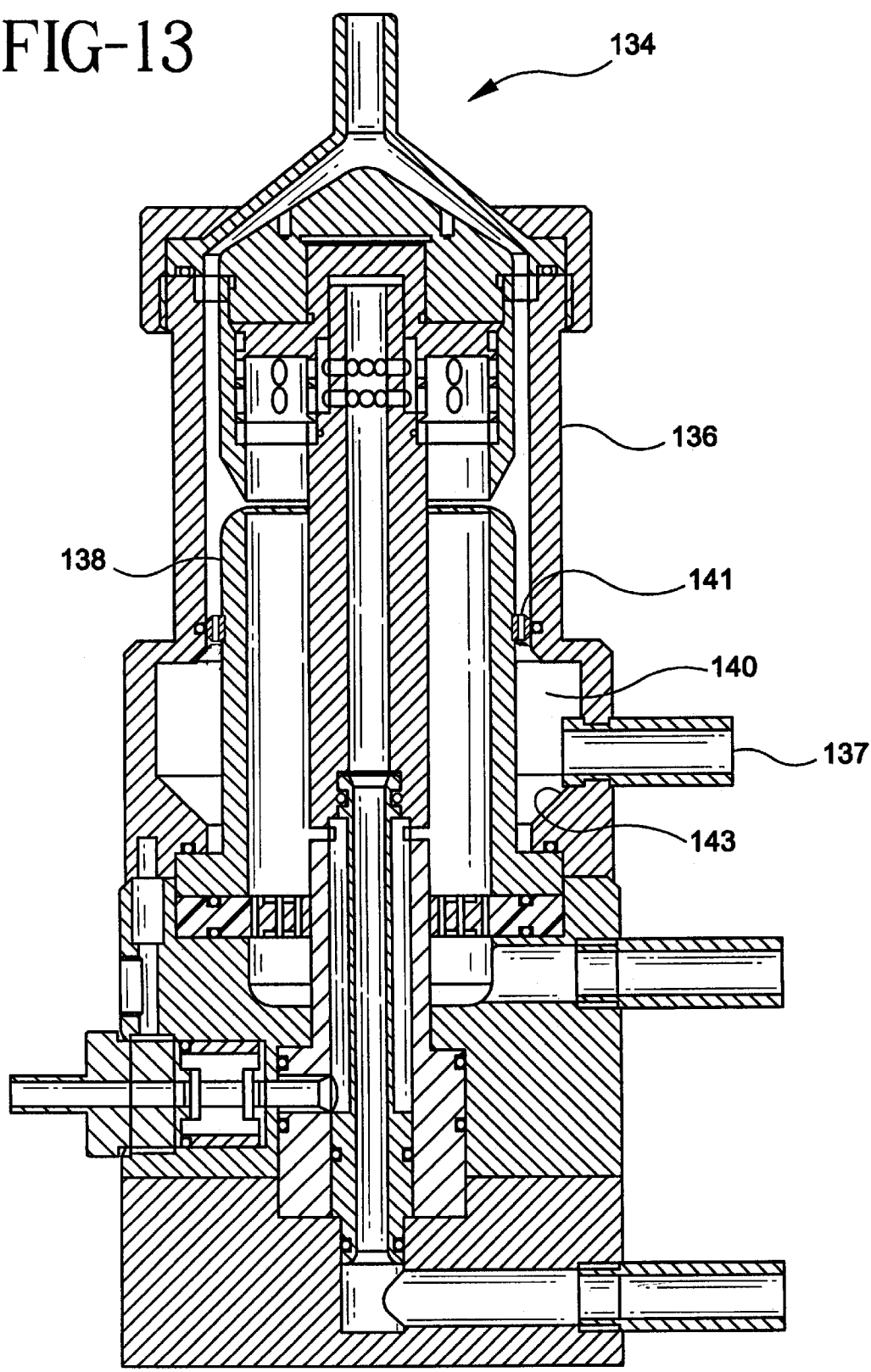
Figure 15:
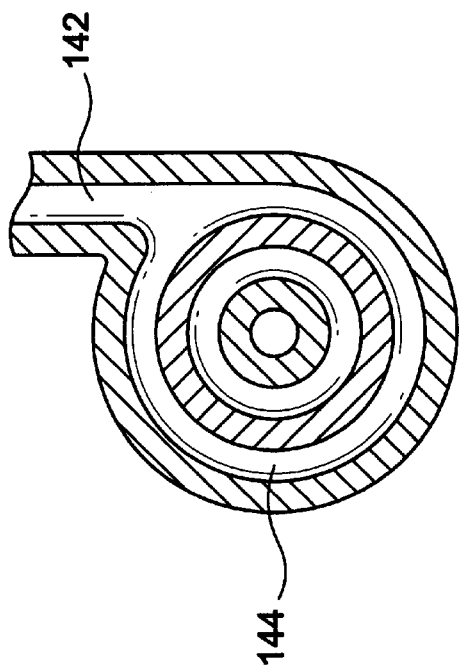
Figure 14:
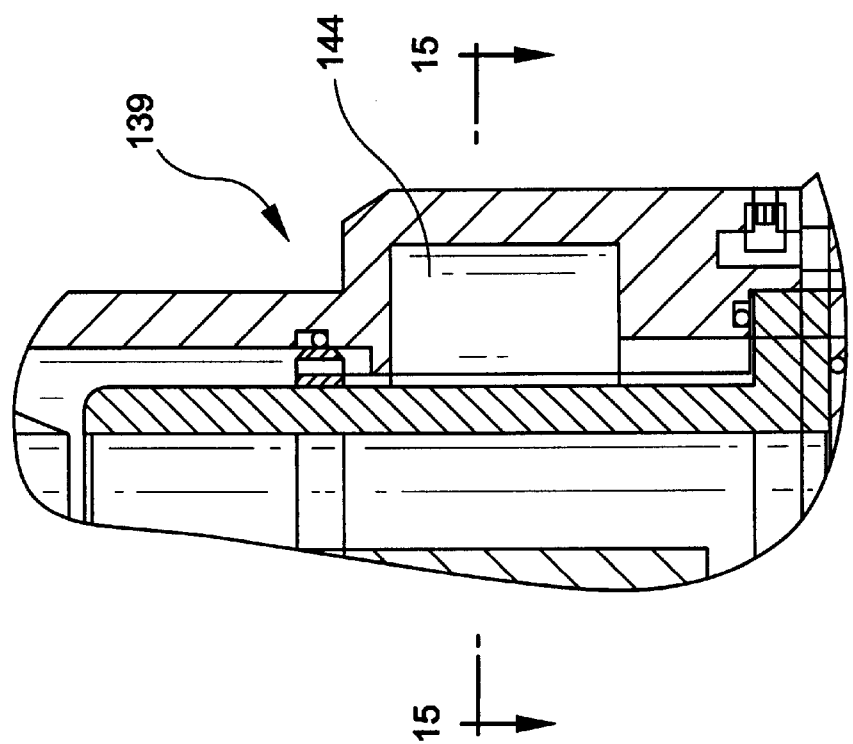

FIG. 9 graphically illustrates transfer function half-widths at different flow ratios;

FIG. 10 schematically illustrates an alternative embodiment DMA;

FIGS. 11 and 12 show an annular flow restricting feature used in the DMA;

FIG. 13 is a sectional view of an alternative DMA incorporating a plenum for receiving excess aerosol that bypasses the merger area; and FIGS. 14 and 15 show a further alternative DMA incorporating a tangential exit port into the bypass system for excess aerosol.

DETAILED DESCRIPTION OF THE PREFERRED EMBODIMENTS

Figure 1:
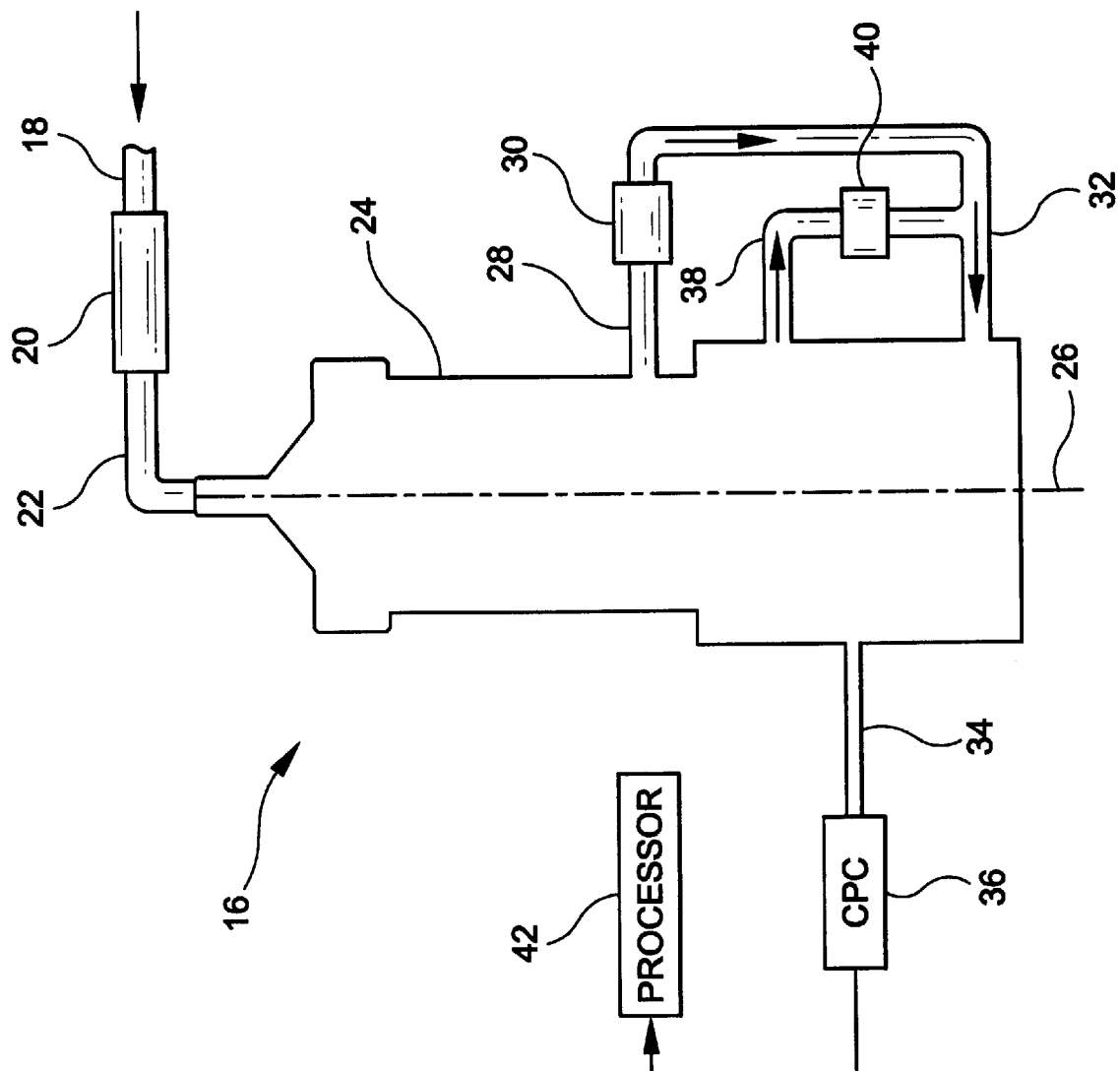
FIG. 1 is a schematic view of an aerosol analyzing system constructed in accordance with the present invention.

Turning now to the drawings, there is shown in FIG. 1 is a system 16 for measuring and classifying particles or other elements suspended in the gaseous medium (usually air) of a polydisperse aerosol. Particles having diameters within a range of about 3–50 nanometers (nm) are of particular interest, and system 16 has several features, discussed below, that enhance the sensitivity and resolution of nanometer particle a detection.

With the system placed in the environment under consideration, e.g., a semiconductor fabrication "clean room", the sample aerosol (ambient air and a suspension of particles) is drawn through an intake line or tubing 18 to a bipolar charger 20 to establish a bipolar-equilibrium charge level on the aerosol particles. From charger 20, the aerosol is drawn into tubing 22, then vertically downward into a differential mobility analyzer (DMA) 24. The sample aerosol is provided in a continuous flow at a constant volumetric rate, e.g., 16.5 liters per minute (lpm).

DMA 24 is cylindrical, substantially radially symmetrical about a vertical axis 26. Inside the DMA, a selected fraction of the aerosol flow, for example about 1.5 lpm, is combined with a flow of clean, filtered sheath air at about 15 lpm. The sample aerosol flow and sheath air flow are laminar, and preferably are combined with little or no turbulence. The remaining, uncombined fraction of the sample aerosol (about 15 lpm) is removed from the DMA via an exit line 28. Further as shown, a filter 30 can be provided along the exit line to remove the suspension, thus to provide clean, filtered air to an input line 32 that provides the sheath air flow to the DMA.

Meanwhile, inside DMA 24, the merged aerosol (i.e., the fraction of the aerosol sample combined with the sheath air) is drawn in a flow past a charged collection electrode.

Particles exhibiting electrical mobilities within a selected range, as determined by the charge level and the flow rate along the electrode, are captured within the electrode and provided via a measurement aerosol output line 34 to a condensation particle counter 36. The remainder of the merged aerosol is provided to an excess air line 38. As shown, a filter 40 can be provided along line 38 so that the expelled aerosol can be recirculated to the DMA as clean sheath air.

Condensation particle counter 36 senses individual particles and accumulates counts of particles which are provided to a microprocessor 42. The microprocessor in turn indicates a concentration of the selected particles within the measurement aerosol, which of course can be used as an indication of the concentration of the selected elements in the sample aerosol.

Figure 2:
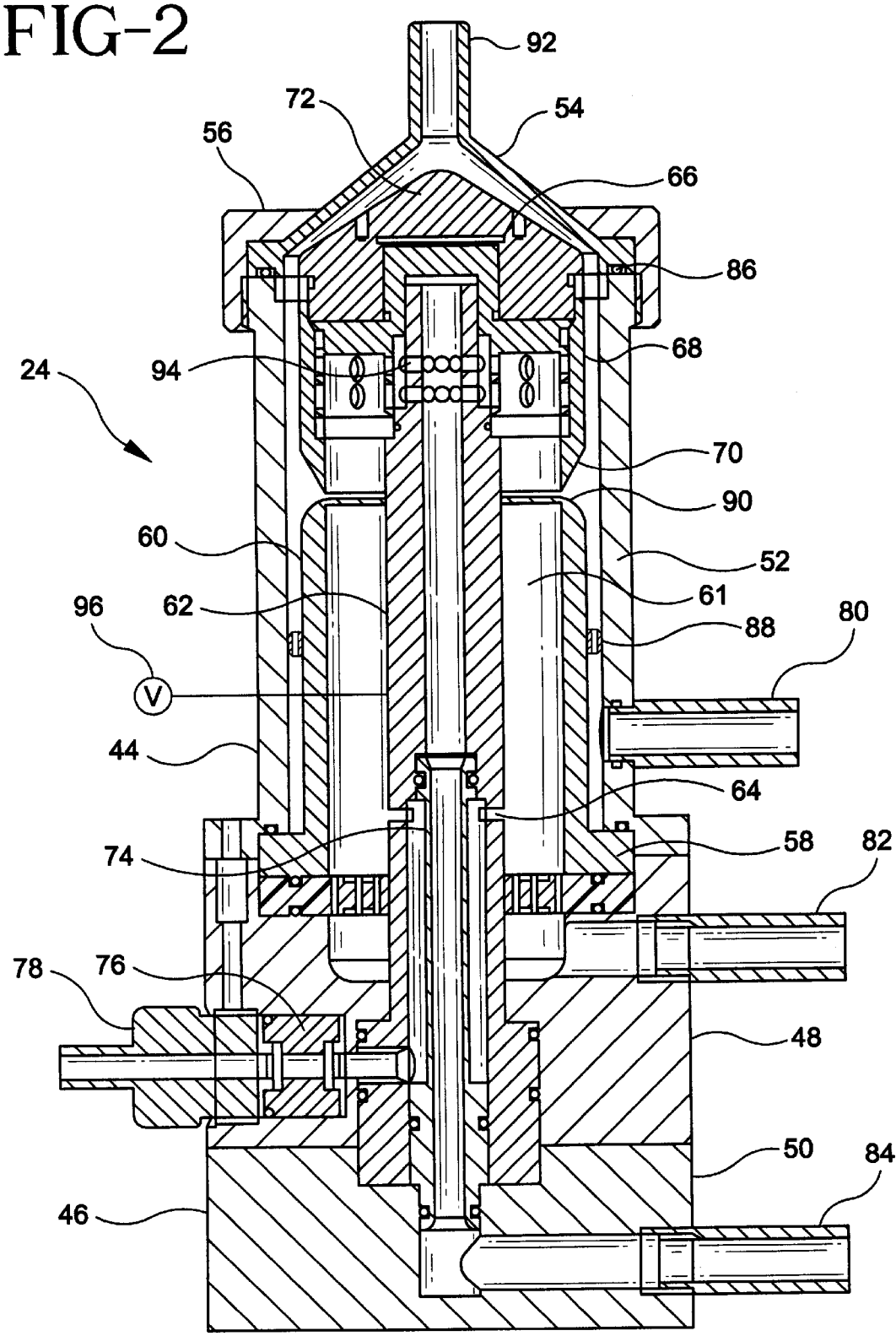
FIG. 2 is a sectional view of a differential mobility analyzer of the system.
Figure 3:
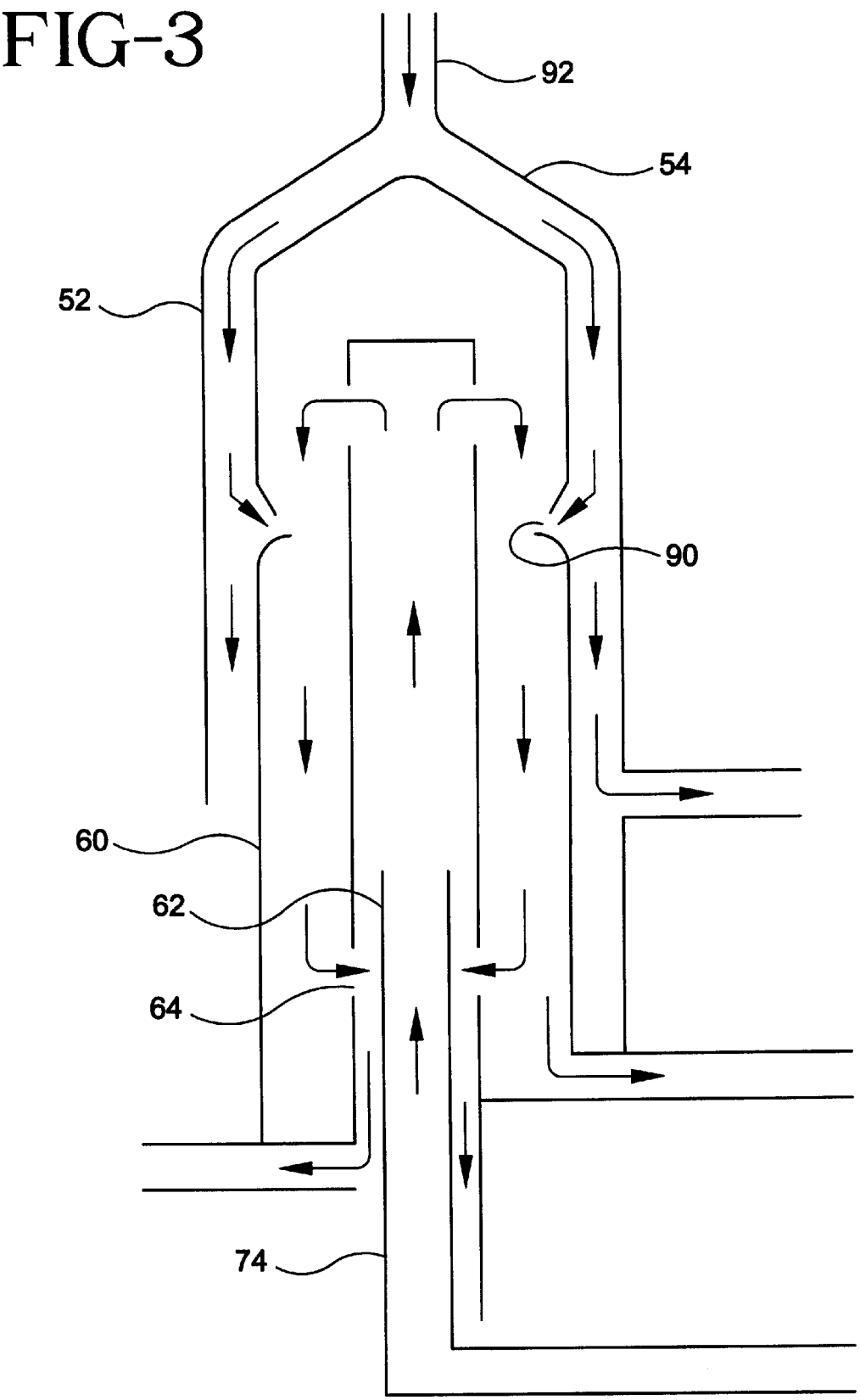
FIG. 3 is a schematic partial view of the DMA, illustrating aerosol and sheath air flows.

FIG. 2 illustrates DMA 24 in greater detail. Essentially, the DMA includes a housing 44 and internal components assembled to form several fluid flow conduits. The intake or receiving conduits include a sample aerosol conduit for receiving the aerosol to be analyzed, and a sheath air conduit for the incoming sheath air flow. In addition, there are three exit conduits for excess sample aerosol, excess merged aerosol, and measurement aerosol, respectively. Housing 44 and the components also cooperate to provide key operative components, primarily the electrodes.

More particularly, the housing includes a base 46 composed of upper and lower cylindrical base segments 48 and 50. The base segments have channels formed therein to accept components or to provide portions of the conduits. An annular outer wall 52, preferably formed of metal, is releasably secured to the base at segment 48 and extends upwardly from the base. At the top of outer wall 52 is a stainless steel cover or cap 54, secured to the outer wall by a threaded clamp 46.

A disk-shaped insulative pad 58 is mounted to base segment 48, and in turn supports an annular outer electrode 60 constructed of stainless steel. An elongate, tubular collection electrode 62 is supported within the base, and extends upwardly beyond the outer electrode. An annular slot or collection aperture 64 is formed through collection electrode 62, along its medial region and more particularly slightly below a midpoint of the electrode. Near the top of tubular electrode 62, several radially extending and circumferentially spaced apart openings extend through the electrode wall, to allow air to flow from within the electrode to its exterior. Vertical openings are formed through the insulative pad to equalize flow, and tend to locate the principal pressure drop and promote laminar flow along the annular region 61 between electrodes 60 and 62.

An electrically insulative retainer 66 surrounds the upper part of electrode 62. An annular stainless steel sleeve 68 with a truncated conical lower edge 70 cooperates with the retainer to releasably fix the collection electrode within the housing. A cover piece or dome 72 formed of stainless steel, with a conical top surface, is mounted over the retainer and cooperates with cap 54 to define part of the sample aerosol conduit.

A tubular flow guide 74, formed of stainless steel, is mounted within electrode 62, extending from a location just above slot 64 downwardly to the bottom of the collection electrode. The flow guide is contiguous with, and thus electrically coupled to, electrode 62. The flow guide and lower portion of the electrode cooperate to provide two coaxial fluid full paths, an inner path for sheath air, and a radially outward annular path for the aerosol under analysis.

An insulator 76 cooperates with the base to electrically isolate the collection electrode, and is removably retained by a metal fitting 78. Openings through fitting 78, insulator 76 and electrode 62 cooperate to provide the measurement aerosol exit conduit. Finally, tubular lines 80, 82 and 84 form part of the conduits for excess sample aerosol, excess merged aerosol and sheath air, respectively. Multiple elastomeric sealing rings, one of which is indicated at 86, are positioned between the more rigid components to form fluid seals.

An annular flow restriction feature 88 is built into the structure of outer electrode 60. Feature 88 preferably is constructed of a high molecular weight plastic, e.g., Delrin (brand) acetal plastic. Multiple, tiny apertures are formed through feature 88. Accordingly, although it permits downward flow of the sample aerosol between electrode 60 and housing outer wall 52, feature 88 restricts fluid flow to insure a substantially uniform velocity distribution circumferentially throughout the space between the wall and the outer electrode. This effectively insures a substantially uniform flow at and near an annular slit 90 formed by the top edge of electrode 60 and the lower edge 70 of annular sleeve 68. Slit 90 can be conveniently thought of as a merger area, where the sheath air and part of the sample aerosol are combined. The slit width, taken in the axial direction, is about 0.030 inches, much less than the width of about 0.5 inches found in previous designs. Th advantage of the significantly reduced widths, and the factors that enable it, are discussed below.

FIGS. 11 and 12 illustrate annular feature 88 in greater detail. A suitable material for forming feature 88 is an acetal plastic, e.g., Delrin (brand) plastic. Ring 88 has an interior diameter of about 1.78 inches and an exterior diameter of 1.986 inches. Thirty-six evenly spaced apart openings, each having a diameter of 0.040 inches (0.038–0.042 inches being suitable), are formed through the ring, each approximately centered between the inner and outer edges. The porosity of annular feature 88 is about 7.4 percent, based on the combined area of the thirty-six openings compared to the total area of feature 88 in planes perpendicular to the central axis, and taking the opening diameter as 0.040 inches. The porosity should be at most about 20 percent, and more preferably is 5–10 percent.

The use of annular feature 88 to restrict flow, as compared to simply narrowing the radial gap width between outer electrode 60 and outer wall 52, has been found considerably more effective in promoting and maintaining laminar flow, particularly by insuring a uniform pressure drop circumferentially about the annular passage. An annular gap, to provide the equivalent uniformity advantage, would be so narrow as to unduly restrict the flow.

A naturally porous material, having a porosity equivalent to that based on the combined area of the openings and the feature area as determined above,, would be a suitable substitute for feature 88.

The characteristic length of DMA 24, i.e., the distance between slit 90 and collection aperture 64, is 50 millimeters. The more laminar flows decrease defusion losses as the aerosol to be measured moves along the annular passage between the entrance slit and the collection aperture or slot. Collection aperture 64 more precisely includes a set of four slots through collection electrode 62, arranged circumferentially about the electrode, with each slot extending in an arc of about 60 degrees. The slot width in the axial direction is about 0.66 inches.

The various fluid flow conduits formed by the housing and interior components can be understood from FIG. 3, when viewed in conjunction with FIG. 2. The sample aerosol enters the housing flowing downwardly through an upper neck 92 (0.250 inch inside diameter) of entrance cap 54, which is centered on vertical axis 26 as are all of the major flow-governing components. Flow of the aerosol is laminar, and remains laminar as it encounters the top surface of cover piece 72 and fans radially outward. Then, the laminar flow proceeds downward along the space between annular sleeve 68 and housing wall 52, toward the merger area, i.e. slit 90. A taper in the fluid conduit formed by cover 54 and dome 72 promotes laminar flow. More particularly, cover 54 is inclined at an angle of about 40 degrees from the horizontal, while dome 72 is inclined at an angle of about 30 degrees from the horizontal, which causes a convergence in the space between these two components in the radially outward direction. The space converges toward about 0.1 inches, to substantially match the radial spacing between sleeve 68 and wall 52.

Meanwhile, filtered, clean sheath air enters the DMA at tubing line 84, proceeds upwardly through the interior of flow guide 74, and above the flow guide proceeds through the interior of collection electrode 62. Near the top of electrode 62, sheath air proceeds radially outward through radial openings 94 to the annular space between electrode 62 and sleeve 68. Then, the sheath air, remaining in a laminar flow, proceeds downwardly towards the merger area. A screen or other smoothing feature can be provided near the top of the collection electrode, to promote a smoother flow at the stage where the ascending sheath air is turned radially outward.

At the merger area, the sheath air is combined with a portion of the sample aerosol. More particularly, it has been found advantageous to combine the flows at a flow ratio of 10:1 in terms of sheath air volume to aerosol volume, more specifically with respective flow rates of 15 liters per minute (lpm) and 1.5 lpm. This combination, conveniently thought of as a merged aerosol, proceeds downwardly along a particle collection region, i.e. the annular space between electrodes 60 and 62 and extending from slit 90 to slot 64.

As the merged aerosol proceeds along the collection region, collection electrode 62 (coupled to a voltage source 96) is maintained at a potential sufficient to provide the desired charge. Outer electrode 60 is coupled to ground. Consequently, oppositely charged particles in the merged aerosol are attracted radially inward to the collection electrode. Particles having the same charge are repelled toward the outer electrode, while neutral particles proceed downward with the prevailing flow. Particles having a high electrical mobility, characteristically the smaller diameter particles, are drawn against electrode 62 before they reach slot 64. Charged particles of lower electrical mobility are carried beyond aperture 64 before they reach electrode 62. However, particles having electrical mobility values (for example in terms of centimeters squared per volt second) within a selected, narrow range, are drawn through aperture 64 into the annular passage between flow guide 74 and electrode 62. The electrical mobility range, which can be predetermined as a function of flow velocity and level of charge to the collection electrode, effectively determines a narrow range of particle size as well.

The narrow range of particles passing through aperture 64, together with a portion of the air or other sheath gas in which they are suspended, are conveniently thought of as a selected aerosol or measurement aerosol, which proceeds downwardly to the lower end of electrode 62, then radially outward along the openings through the electrode, insulator 76 and fitting 78. At this point, the measurement aerosol is provided to a condensation particle counter or other instrument capable of accumulating particle counts or otherwise determining particle concentrations. Alternative concentration measuring devices include aerosol electrometers and photometers. Certain particle sampling devices, such as filters, electrostatic precipitation samplers, thermal precipitation samplers and low-pressure impactors, also may be used.

Several features of housing 44 and its interior components are particularly well suited for the measurement and classification of nanometer aerosols, e.g. with element diameters in the range of about three to about 50 nanometers. One of these is the radial symmetry of the sample aerosol conduit formed by cap 54 including neck 92, cover piece 72, sleeve 68 and the upper portion of housing wall 52. These components form an initial intake portion of the conduit along and centered on axis 26, a concentric annular portion, and an intermediate portion that accommodates radially outward and slightly downward flow from the intake to the annular portion. The coaxial arrangement, as compared to conventional arrangements with radially off-set aerosol inputs, more readily establishes and maintains laminar flow. As a result, the sample aerosol conduit can be substantially shorter than similar conduits in prior devices. The shorter path toward the merger area reduces the amount of particle diffusion due to Brownian motion. With fewer particles lost, detection is more sensitive. Also, resolution is higher, because there is less broadening of the transfer function from particle diffusion. In actual practice, the aerosol sample conduit or transport path has been reduced to less than half of the length formerly required.

Aerosol losses are further reduced by provision of an excess flow of the sample aerosol. As noted above, only a portion of the aerosol flow travels through slit 90 for merger with the sheath air. The remainder of the flow instead continues downwardly along an annular bypass conduit between outer electrode 60 and housing wall 52, beyond flow restriction feature 88 and out of the DMA through tubing 80. Preferably, most of the sample aerosol bypasses slit 90. For example, a satisfactory flow ratio is 10:1 in terms of the bypass flow as compared to the flow through the slit for combination with sheath air. Specifically, given the 1.5 lpm flow for aerosol through the slit as mentioned above, the bypass flow is 15 lpm, for a total incoming sample aerosol flow of 16.5 lpm.

Thus, the inflow of the sample aerosol along neck 92 is considerably more than that needed for combination with sheath air and eventual measurement. Because of the excess intake, sufficient volume of the aerosol is provided through slit 90, without requiring an unduly high linear flow of velocity or pressure drop through what would be a considerably narrower conduit. In particular, the gap width or radial dimension of the annular gap between outer wall 52 and sleeve 68 is at least 0.05 inches, and more preferably is at least 0.10 inches. The result is a maintenance of laminar flow in combination with a short residence time of the aerosol within the sample aerosol conduit, resulting in a further, substantial reduction in particle diffusion loss. In practice, transit time through the sample aerosol conduit has been cut to as little as one-tenth the previous requirement. This has reduced diffusion losses to one-third of previous losses, at a nominal diameter of 3 nm.

Figure 4:
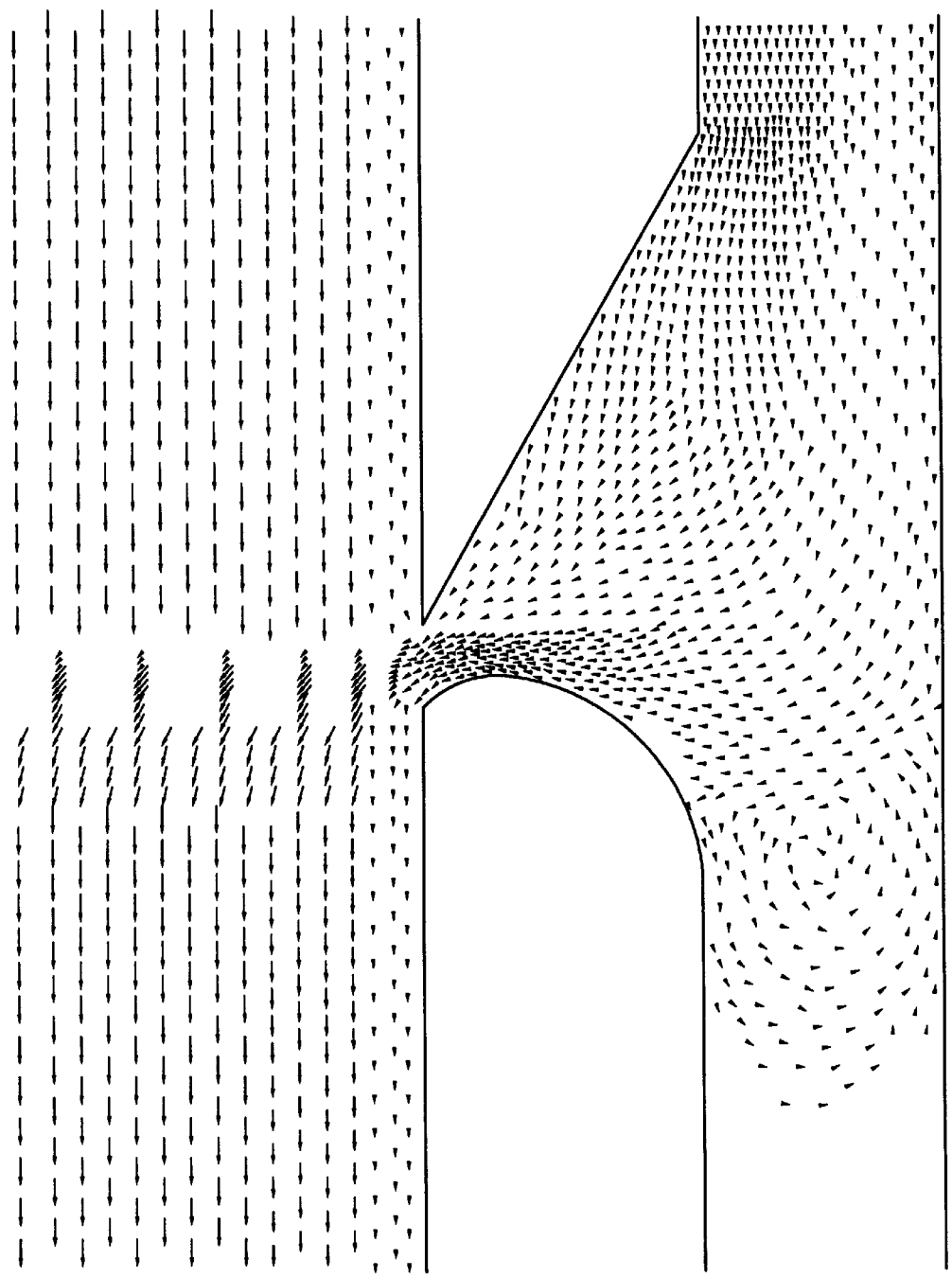
FIG. 4 is an enlarged partial view of the DMA, illustrating flow patterns near a classifying region inlet.

As best seen in FIG. 4, the lower edge of sleeve 68 and the upper edge of electrode 60 are aerodynamically designed to promote a smooth, fluid flow through slit 90. In particular, lower edge 70 is beveled to a knife edge, while the upper edge of the electrode is rounded, formed with a relatively large radius (0.118 inches) on the radially outward side and a much shorter radius (0.024 inches) near the radially inward edge. In particular, the beveled surface is relatively steep, inclined from the central axis (vertical in FIG. 4) at most about 45 degrees, and more preferably at most about 30 degrees. The arrows show the flow pattern. This design also achieves a good matching of the sheath air flow and the flow of the aerosol through the slit. Flow recirculation near the slit is eliminated by a combination of this aerodynamic design and the bypass conduit for excess aerosol. With no flow recirculation, the useable range of flow ratios is expanded, making it possible to achieve high resolution measurements with flow ratios of 20:1 or higher, not possible in previous designs.

Figure 5:
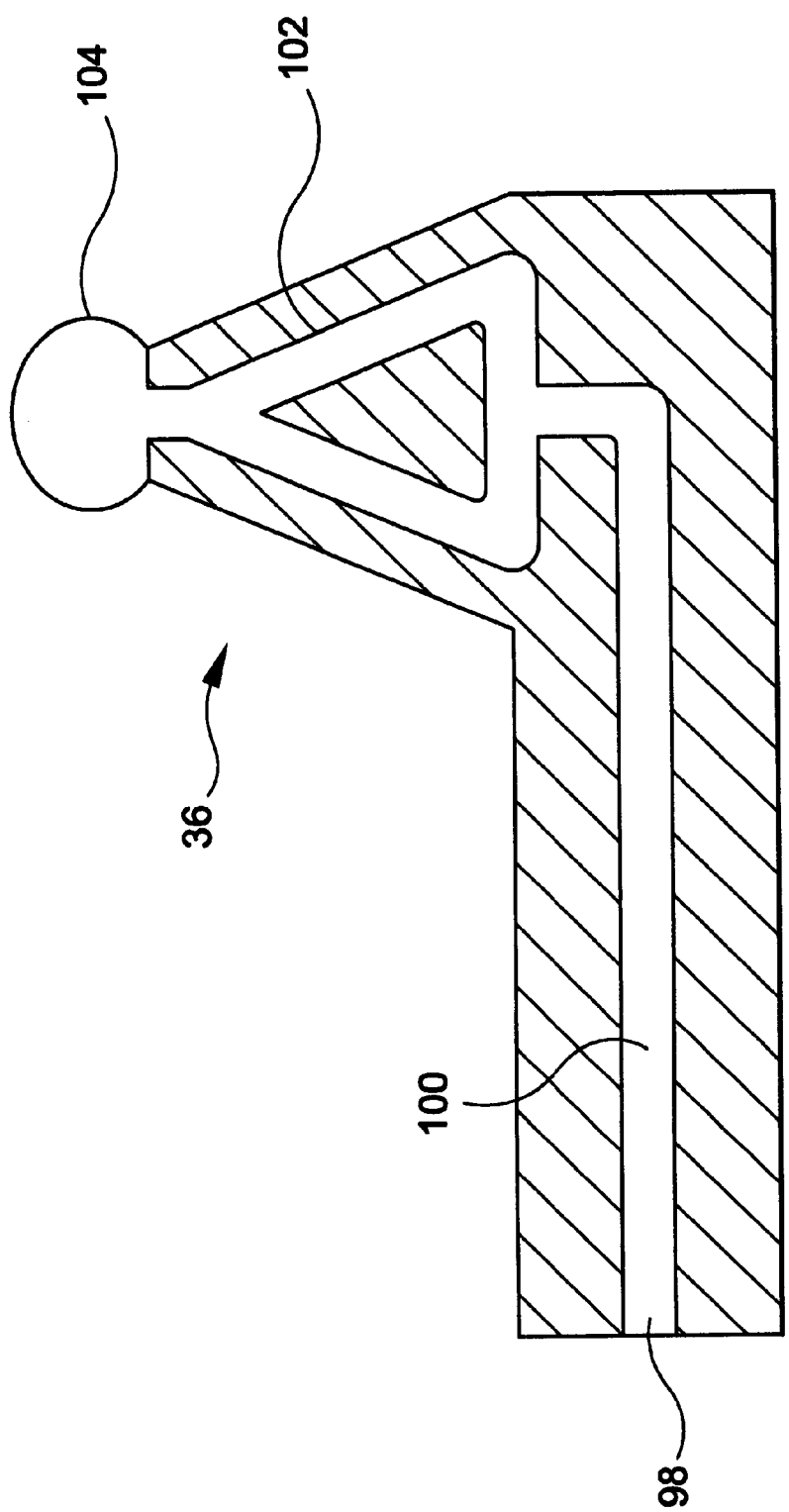
FIG. 5 is a schematic view of a condensation particle counter of the system.

Another improvement with respect to prior devices is the substantial reduction in the axial width of slit 90. The preferred width, vertically as viewed in FIG. 5, is about 0.030 inches, preferably within a range of 0.026–0.034 inches, and less preferably within a range of 0.02–0.04 inches. In prior designs, the width is considerably greater, for example on the order of about 0.5 inches. The substantial bypass flow, and the aerodynamic design near slit 90, enable the considerable narrowing of the slit. The narrower slit prevents undue electric field penetration into the slit opening. Such penetration causes electric field distortions in the classifying region near the slit. This problem becomes more severe as the length of the classifying region is reduced, as is the case when measuring nanometer particles. The narrow slit eliminates this problem.

Yet another advantage of DMA 24 is a more compact design, made possible by the introduction of the sample aerosol and sheath air in opposite vertical directions. In addition to being more compact, this approach allows initial incoming flows of the sample aerosol and sheath air to be centered and along axis 26. Both flows can proceed along the axis, then fan radially outward into the annular, downward flow toward the merger area. There is no need to offset either flow from the center, which in both cases provides more laminar flows.

Part of the vertically upward sheath air flow is accommodated by flow guide 74. The measurement aerosol proceeds downwardly, along the surrounding annular path. Both the interior flow guide path and the surrounding annular path are made large enough to accommodate their respective flows without a significant pressure drop. For example, the interior diameter of the flow guide is about 0.18 inches, while the radial dimension of the surrounding annular space is at least about 0.10 inches.

Another advantage of the present design is the downward extension of collection electrode 62 beyond aperture 64, i.e. the positioning of the collection aperture medially along the electrode. The result is a uniform electrical field across the entire classifying region (i.e. from slit 90 to aperture 64). Unwanted electrical field fringing near the collection aperture is eliminated. More generally, the electrical field fringing is minimized satisfactorily if collection aperture 64 is spaced apart upstream by an axial distance at least about two millimeters from the downstream end of collection electrode 62.

One consequence of this arrangement is that electrode 62 remains charged a substantial distance downstream of collection aperture 64. To insure that this does not cause electrostatic loss of particles from the measurement aerosol, flow guide 74 is electrically coupled to the collection electrode, and thus maintained at the same level of charge. This minimizes the chance for electrostatic loss as the measurement aerosol proceeds to its exit conduit.

The exiting measurement aerosol is provided to condensation particle counter 36. This device, sometimes called a condensation nucleus counter, is seen in more detail in FIG. 5, and can be similar to the device described in U.S. Pat. No. 4,790,650 (Keady). Briefly, the measurement aerosol enters an inlet 98 and proceeds through a saturation zone 100, where butyl alcohol or another volatile liquid is continually evaporated into a gas stream. A gas stream, substantially saturated, proceeds into a condensation zone 102, where the aerosol is cooled sufficiently to cause the volatile liquid to condense onto the suspended particles, in effect "growing" each particle to a larger effective size for easier detection. The enlarged particles proceed to an optical detection zone 104, where individual particles pass through and momentarily interrupt a laser beam, thus to generate a particle recognition signal and add to an accumulated particle count. For an aerosol sample of a given volume, the accumulated count indicates the concentration of particles suspended in the aerosol.

Figure 6:
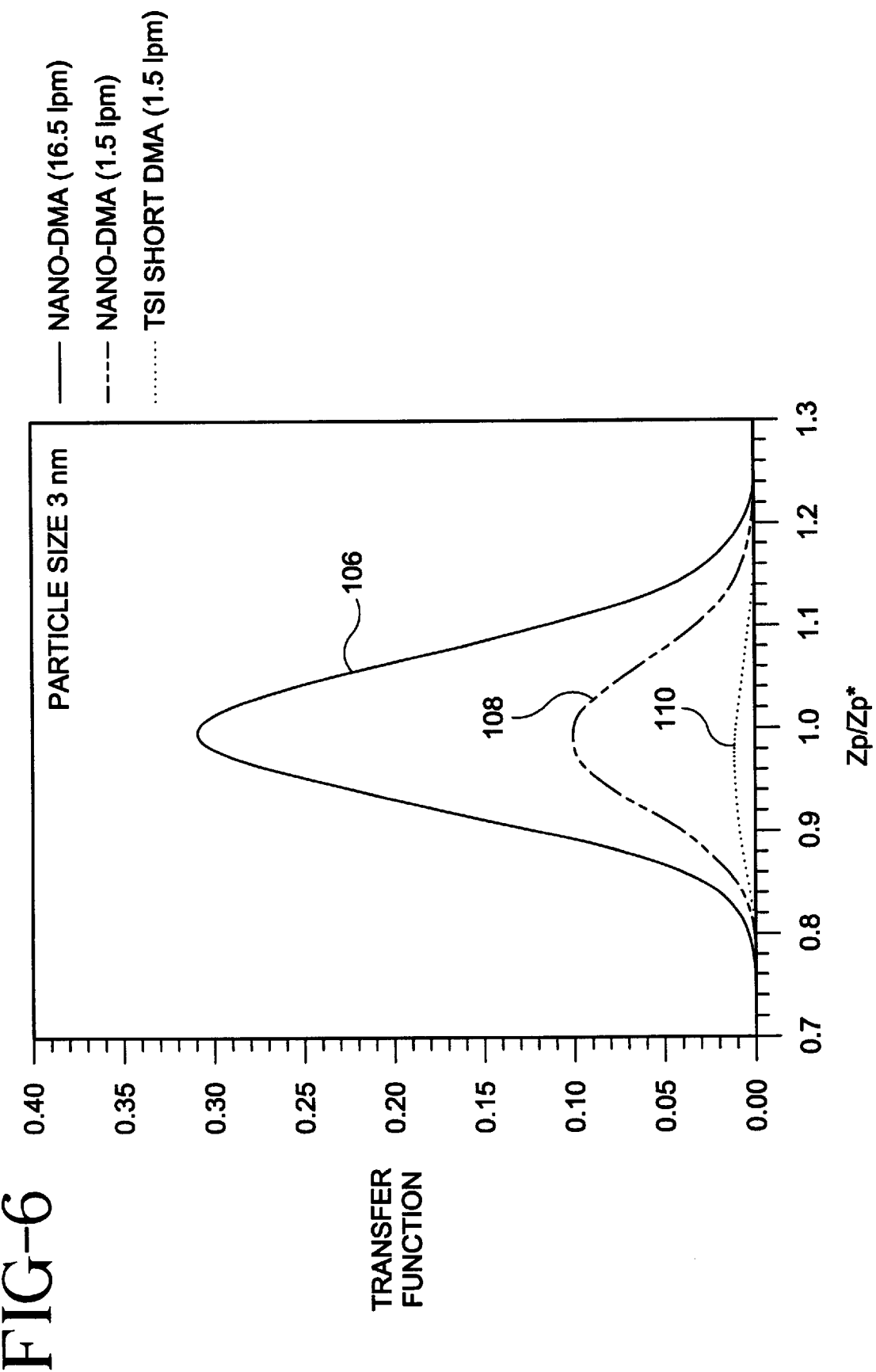
FIG. 6 is a chart illustrating transfer functions corresponding to different aerosol flow rates.

FIG. 6 shows the transfer functions of aerosols measured in system 16, with one measurement from a prior design DMA, over a range of actual/nominal diameters, for a nominal particle diameter of 3 nanometers. Curve 106 represents an aerosol flow rate of 16.5 lpm. Curve 108 reflects an aerosol flow rate of 1.5 lpm. Curve 110 represents the prior DMA, and a flow rate of 1.5 lpm. In all cases, this sheath flow rate is 15.0 lpm. Curve 110 relates to the TSI-short DMA, found to be the best performing DMA of previous designs in the study mentioned above. The transfer function plots demonstrate that system 16 affords a substantial improvement in detection sensitivity. Further substantial improvement and sensitivity is obtained by incorporating the excess aerosol flow described above, in particular a three-fold increase in sensitivity at the 3 nanometer diameter.

Figure 7:
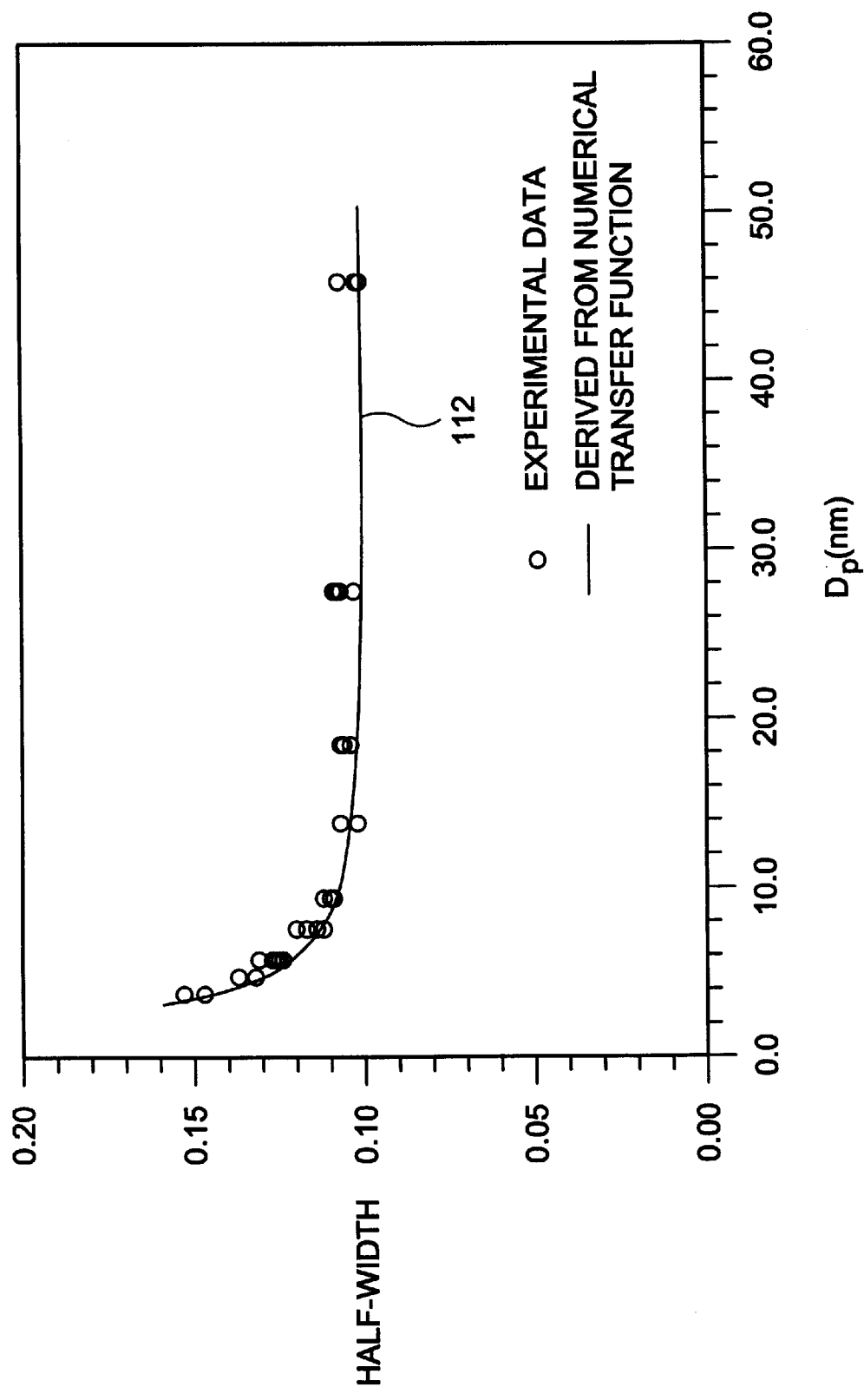
FIG. 7 is a graphical comparison of numerically derived and experimental transfer function half-width data.

In the chart of FIG. 7, a line 112 representing numerical transfer function data is compared with circles representing experimental results. Transfer function half-widths are plotted as a function of particle size, for a flow ratio often (15.0 sheath vs. 1.5 lpm measured aerosol). Higher half-width values indicate higher resolution. The agreement between the numerical and experimental results extends over the entire particle size range shown.

Figure 8:
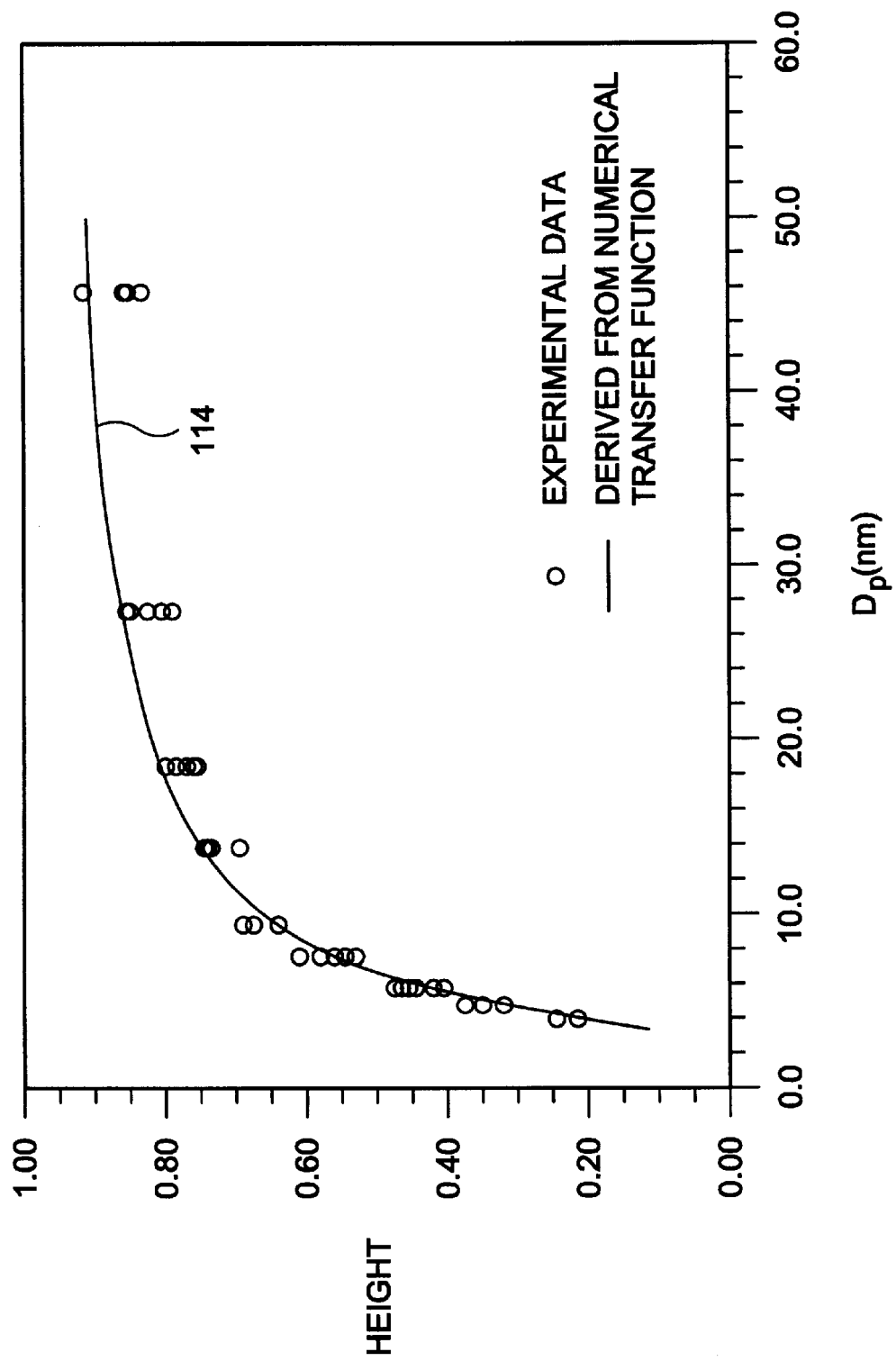
FIG. 8 is a graphical comparison of numerically derived and experimental transfer function height data.

FIG. 8 is a chart comparing numerically derived transfer function heights (line 114) and experimental values indicated by the circles. The improved transfer function heights indicate improved detection sensitivity.

The chart of FIG. 9 shows transfer function half-width values as a function of particle size for several different flow ratios, including 7.5:1.5 (line 116), 30:1.5 (line 118), and 30:1 (line 120). Under ideal conditions, the transfer function half-width in these cases would be 0.2, 0.05 and 0.033, respectively. These plots demonstrate that resolution is increased using a smaller aerosol/sheath flow ratio.

FIG. 10 schematically illustrates an alternative embodiment differential mobility analyzer 124, similar to DMA 24 except that a collection aperture 126 is provided near the lower end of a collection electrode 128. Below the collection electrode, an electrically insulative tube 130 and an electrically insulative flow guide 132 are provided for conducting the sheath flow and the measurement aerosol as previously described. The insulative tubing provides a greater degree of electrical isolation of the charged collection electrode, with respect to the exterior housing components. The disadvantage of this approach is the introduction of a fringing field effect near collection aperture 126.

FIG. 13 illustrates an alternative embodiment DMA 134, similar to DMA 24 in most respects. One exception is an annular plenum 140 in fluid communication with the annular passage for excess aerosol between an outer wall 136 and an outer electrode 138, i.e., the components equivalent to 52 and 60 in FIG. 2. Plenum 140 is disposed just below an annular flow restriction feature 141 similar to feature 88. Thus, the plenum provides a considerably increased annular volume in the annular passage for excess aerosol. Pressure tends to equalize rapidly throughout the plenum, counteracting any tendency for pressure differences in areas of the plenum near an exit line 137 for excess aerosol (equivalent to line 80 in FIG. 2), and areas within the plenum remote from the exit.

FIG. 14 is a partial sectional view of an alternative DMA 139, with an enlargement or plenum 144, which is similar to plenum 140 except that it is rectangular in cross section, lacking the downward convergence 143 below plenum 140.

FIG. 15 illustrates alternative DMA 139 in section, taken along the line 15—15 in FIG. 14, illustrating an alternative construction, namely an excess aerosol exit conduit 142 that extends tangentially, rather than radially, away from annular plenum 144 for the excess aerosol. If desired, plenum 144 can be provided with a plenum convergence as in FIG. 13. The tangential exit tends to promote a less turbulent flow of the excess aerosol out of the DMA. Thus, the tangential exit, like plenum 140, contributes to a more uniform and less turbulent flow of excess aerosol throughout the bypass region, including that part of the region upstream of the annular flow restriction feature and near the merger area.

Thus, in accordance with the present invention, nanometer aerosols can be measured and classified with enhanced sensitivity and higher resolution. Improved laminar flows and higher volumetric flow rates, due to an aerosol bypass conduit for removing the excess aerosol, decrease the residence time of the aerosol along the aerosol sample conduit, thus reducing diffusion losses from Brownian motion. The interior, tubular collection electrode is lengthened to enhance electrical field uniformity along the collection region, and the entrance slit to the collection region is considerably narrowed, with both enhancements eliminating unwanted electrical field effects. The collection electrode is tubular to form a conduit for incoming sheath air, providing a more compact design and further enhancing laminar flows. A tubular flow guide simultaneously directs sheath air and the measurement aerosol, and is charged to the level of the collection electrode to avoid electrostatic losses in the measurement aerosol.

What is claimed is:

1. An apparatus for classifying a polydisperse aerosol based on the electrical mobility of particles suspended therein; including:
    a sample aerosol conduit adapted to receive a sample aerosol consisting essentially of a polydisperse suspension of particles in a gaseous medium, and to conduct the sample aerosol in a substantially non-turbulent flow toward a merger area;
    a sheath gas conduit adapted to conduct a filtered sheath gas in a substantially non-turbulent flow toward the merger area, wherein the sample aerosol conduit and the sheath gas conduit are open to the merger area;
    a particle segregation device in fluid communication with the merger area to receive a merged aerosol comprising the sheath gas and a first portion of the sample aerosol, and further adapted for segregating the particles suspended in the merged aerosol according to their electrical mobility, to provide a selected aerosol consisting essentially of selected ones of the particles that exhibit electrical mobilities within a selected range;
    an aerosol bypass conduit in fluid communication with the sample aerosol conduit, for receiving a second portion of the sample aerosol proximate the merger area and conducting the second portion of the sample aerosol away from the particle segregation device; and
    a flow restricting feature comprised of a body having passages therethrough, disposed in the aerosol bypass conduit at a location downstream of the merger area, for restricting fluid flow at said location and thereby tending to equalize a flow velocity of the sample aerosol through the sample aerosol conduit upstream of the restricting feature.

2. The apparatus of claim 1 wherein:
said flow restricting feature has a porosity, in terms of a ratio of the combined area of the passages to the area of the flow restriction feature taken in planes perpendicular to a direction of the fluid flow at said location, of at most about 20 percent.

3. The apparatus of claim 2 wherein:
said porosity is in the range of about 5 percent to about 10 percent.

4. The apparatus of claim 2 wherein:
said passages comprise a series of uniformly sized and uniformly spaced apart openings through said body.

5. The apparatus of claim 1 wherein:
said aerosol bypass conduit at said location is annular, and said body is annular and spans a radial width of the aerosol bypass conduit.

6. The apparatus of claim 1 wherein:
a sample volumetric flow rate of the sample aerosol through the sample aerosol conduit is at least about ten times a first portion volumetric flow rate of said first portion of the sample aerosol through the sample aerosol conduit.

7. The apparatus of claim 1 wherein:
a sheath gas volumetric flow rate of the sheath gas through the sheath gas conduit is greater than a first portion volumetric flow rate of said first portion of the sample aerosol through the sample aerosol conduit.

8. The apparatus of claim 1 wherein:
said sheath gas flow rate is about ten times the first portion flow rate.

9. The apparatus of claim 1 wherein:
said non-turbulent flows of the sample aerosol and the sheath gas further are at constant volumetric flow rates.

10. The apparatus of claim 1 wherein:
said particle segregation device includes a passage to accommodate a flow of the merged aerosol therethrough, an electrically conductive electrode disposed along the passage, electrically biased to attract oppositely charged ones of said particles suspended in the merged aerosol flowing along the electrode, and a collection aperture formed in the electrode for receiving said selected ones of the particles.

11. The apparatus of claim 10 wherein:
the aperture is formed through the electrode wall along a medial region of the electrode.

12. The apparatus of claim 1 further including:
a wall between the sample aerosol conduit and the sheath gas conduit, wherein said merger area comprises a slit through the wall.

13. The apparatus of claim 12 wherein:
said slit has a uniform width of about 0.02–0.04 inches.

14. The apparatus of claim 1 wherein:
said sample aerosol conduit and sheath gas conduit include respective coaxial and side-by-side circular cylindrical portions.

15. The apparatus of claim 14 wherein:
the sample aerosol and sheath gas are conducted toward their respective circular cylindrical portions in opposite directions axially of the cylindrical portions.

16. The apparatus of claim 14 wherein:
the particle segregation device includes an elongate electrically conductive tubular electrode adapted to accommodate a flow of the sheath gas toward its associated one of the circular cylindrical portions.

17. The apparatus of claim 16 further including:
an aperture in the tubular electrode for receiving said selected aerosol into the electrode.

18. The apparatus of claim 17 further including:
an electrically conductive flow guide inside of the electrode, extending downstream from the aperture and electrically coupled to the electrode.

19. The apparatus of claim 18 wherein:
the flow guide is tubular and adapted to accommodate a flow of the sheath gas therethrough, while accommodating an axial flow of the selected aerosol between the flow guide exterior and the electrode.

20. A system for determining a concentration of the selected particles, including the apparatus of claim 1 and further including:
an aerosol concentration determining device coupled to receive the selected aerosol from the particle segregation device.

21. The system of claim 20 wherein:
said aerosol concentration determining device comprises one of: a condensation particle counter, an aerosol electrometer, a photometer, a filter, an electrostatic precipitation sampler, a thermal precipitation sampler, and a low-pressure impactor.

22. The system of claim 21 further including:
a charging device along the sample aerosol conduit.

23. The apparatus of claim 1 further including:
a recycling means in fluid communication with the aerosol bypass conduit and with the sheath gas conduit, for receiving the second portion of the sample aerosol, filtering the second portion of the sample aerosol to generate a filtered sheath gas, and supplying the filtered sheath gas to the sheath gas conduit.

24. The apparatus of claim 23 wherein:
said recycling means comprises a recycling conduit and a filter disposed along the recycling conduit.

25. An apparatus for classifying an aerosol, including:
first and second substantially radially symmetrical conduits for conducting, respectively, a sample aerosol and a sheath gas in substantially non-turbulent flows toward a merger area, wherein said first conduit includes a first annular segment, said second conduit includes a second annular segment substantially coaxial with the first annular segment, and the first and second annular segments are open to said merger area;
a cylindrical wall between the first and second annular segments, wherein the merger area comprises a slit through the cylindrical wall with a width in the axial direction of about 0.02–0.04 inches; and
a particle segregation device in fluid communication with the merger area and adapted to receive a merged aerosol comprising the sheath gas and at least a first portion of the sample aerosol, and further adapted to segregate particles suspended in the merged aerosol according to their electrical mobility, thus to provide a measurement aerosol consisting substantially of the particles exhibiting electrical mobility values within a selected range.

26. The apparatus of claim 25 wherein:
the first conduit conducts the sample aerosol to the merger area, the second conduit conducts the sheath gas to the merger area, and the first annular segment surrounds the second annular segment.

27. The apparatus of claim 25 wherein:
said particle segregation device includes an elongate, tubular, electrically conductive electrode substantially coaxial with the first and second annular segments, said electrode including an aperture formed therethrough along a medial region thereof, for receiving the measurement aerosol into the electrode as the merged aerosol flows along the electrode.

28. The apparatus of claim 27 further including:
an elongate, cylindrical and electrically conductive flow guide contained within the electrode, extending downstream from the aperture, and electrically coupled to the electrode.

29. The apparatus of claim 28 further including:
an aerosol bypass conduit in fluid communication with the first conduit for receiving a second portion of the sample aerosol proximate the merger area and conducting the second portion away from the particle segregation device whereby the second portion remains separate from the sheath gas.

30. The apparatus applies in 29 wherein:
said first portion of the sample aerosol is conducted through the first conduit at a first volumetric flow rate at most about 1/10th of a second volumetric flow rate at which the second portion of sample aerosol is conducted through the first conduit.

31. The apparatus of claim 30 further including:
a flow restricting feature in the bypass conduit downstream of the merger area, adapted to restrict fluid flow and thereby tending to equalize a flow velocity of the sample aerosol throughout the first annular segment upstream of the restricting feature.

32. The apparatus of claim 25 wherein:
said first conduit further includes a first central intake segment accommodating flows along an axis, and a first intermediate segment accommodating radially outward flows from the first intake segment to the first annular segment;
said second conduit further includes a second intake segment accommodating flows along said axis, and a second intermediate segment accommodating radially outward flows from the second intake segment to the second annular segment;
the first and second annular segments are substantially centered on said axis; and
the substantially non-turbulent flows in the first and second annular segments and in the first intake segment occur in a first axial direction, and the substantially non-turbulant flows in the second intake segment occur in a second axial direction opposite the first axial direction.

33. An apparatus for segregating polydisperse particles suspended in a gaseous medium, including:
a passageway having an entrance for receiving a polydisperse aerosol;
an elongate, electrically conductive electrode in the passageway, disposed substantially parallel to an axial direction of aerosol flow through the passageway, said electrode being electrically biased to attract oppositely charged suspended particles as the polydisperse aerosol flows through the passageway;

a collection aperture formed through the electrode at a location spaced apart upstream at least about 2 mm from a downstream end of the electrode, for receiving a selected aerosol for passage therethrough, said selected aerosol containing particles substantially limited to the suspended particles that exhibit electrical mobility values within a selected range.

34. The apparatus of claim 33 wherein:

said collection aperture is disposed along a medial region of the electrode.

35. The apparatus of claim 34 wherein:

said passageway is cylindrical, and said elongate, electrically conductive electrode is tubular and substantially coaxial with the passageway.

36. The apparatus of claim 35 further including:

an electrically conductive, elongate and tubular flow guide disposed within the tubular electrode, electrically coupled to the tubular electrode and extending downstream from the collection aperture.

37. The apparatus of claim 36 further including:

a sample aerosol conduit for conducting the polydisperse aerosol in a substantially non-turbulent flow toward the passageway entrance;

a sheath gas conduit for conducting a filtered sheath gas in a substantially non-turbulent flow toward the passageway entrance, wherein the conduits are open to a merger area proximate the passageway entrance at which the sheath gas and at least a first portion of the sample aerosol are combined.

38. The apparatus of claim 37 wherein:

an interior passage through the flow guide forms a portion of the sheath gas conduit.

39. A system for determining a concentration of the selected particles, including the apparatus of claim 38 and further including:

an aerosol concentration determining device coupled to receive the measurement aerosol after its passage through the collection aperture.

40. The system of claim 39 wherein:

said aerosol concentration determining device comprises one of: a condensation particle counter, an aerosol electrometer, a photometer, a filter, an electrostatic precipitation sampler, a thermal precipitation sampler, and a low-pressure impactor.

* * * * *